United States Patent
Yamashita et al.

(10) Patent No.: US 7,122,062 B2
(45) Date of Patent: Oct. 17, 2006

(54) HAIR DYE COMPOSITION

(75) Inventors: Takahiro Yamashita, Yokohama (JP); Kazuya Shibata, Yokohama (JP); Tetsuya Kambe, Tokyo (JP); Katsuo Hashimoto, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 144 days.

(21) Appl. No.: 10/722,546

(22) Filed: Nov. 28, 2003

(65) Prior Publication Data

US 2004/0103488 A1 Jun. 3, 2004

(30) Foreign Application Priority Data

Nov. 27, 2002 (JP) ............................. 2002-344180
Jul. 29, 2003 (JP) ............................. 2003-281973

(51) Int. Cl.
*A61K 7/13* (2006.01)

(52) U.S. Cl. .................. 8/405; 8/406; 8/540; 8/581; 8/606; 8/611

(58) Field of Classification Search .................. 8/405, 8/406, 540, 581, 606, 611
See application file for complete search history.

(56) References Cited

U.S. PATENT DOCUMENTS 6,540,791 B1 * 4/2003 Dias ............................... 8/111

FOREIGN PATENT DOCUMENTS

| JP | 59-106413 | | 6/1984 |
|---|---|---|---|
| JP | 63-174917 | | 7/1988 |
| JP | 03-261709 | | 11/1991 |
| JP | 05-085918 | * | 4/1993 |
| JP | 09-249537 | | 9/1997 |
| JP | 09-255541 | | 9/1997 |
| JP | 10-025230 | | 1/1998 |
| JP | 11-180837 | | 7/1999 |
| JP | 2001-122743 | | 5/2001 |

OTHER PUBLICATIONS

Tomiyuki et al. JP 05-085918, Apr. 1993. (English abstract).*

* cited by examiner

*Primary Examiner*—Eisa Elhilo
(74) *Attorney, Agent, or Firm*—Fei-Fei Chao; Andrews Kurth LLP

(57) ABSTRACT

An objective of the invention is to provide a hair dye composition having sufficient decolorizing performance and dying performance without exhibiting any irritative odor, and also having an ability of imparting the hairs with an excellent smoothness.

The aspect of the invention is a hair dye composition comprising:
  a first agent containing an alkanolamine and an oxidation dye; and,
  a second agent containing an oxidant,
  wherein a higher alcohol and a quaternary ammonium salt cationic surfactant are contained in the first agent and/or the second agent;
  wherein the molar ratio of the higher alcohol to the quaternary ammonium salt cationic surfactant is in the range of 3 to 15.

In the composition described above, it is preferable that substantially no ammonia is contained.

13 Claims, 3 Drawing Sheets

HAIR DYE COMPOSITION

RELATED APPLICATIONS

This application claims from priority Japanese Patent Application No. 2002-344180 filed on Nov. 27, 2002 and Japanese Patent Application No. 2003-281973 filed on Jul. 29, 2003 which are incorporated herein by reference.

FIELD OF THE INVENTION

The present invention relates to a hair dye composition and, in particular, to an improved of its performance.

BACKGROUND OF THE INVENTION

Recently, a demand of changing the color of hairs to a lighter color is increased in response to the change in the consumer's mind, resulting in an expansion of the hair dye market.

A hair dye consists of a first agent containing an alkaline agent and an oxidation dye and a second agent containing an oxidant, and is used first by mixing the first and second agents upon coloring operation, and then applied onto hairs, allowed to stand, and then rinsed (see FIG. 1).

Conventionally, ammonia is employed usually as an alkaline agent. While the ammonia has sufficient decolorizing performance, dying performance and color-lasting performance, it exhibits an intense irritative odor, which gives a substantial discomfort upon coloring operation, sometimes causes an eye irritation. It also causes a stiffness on the hair occasionally after the coloring operation.

Accordingly, it was attempted to use an alkali having a reduced irritative odor instead of the ammonia. For example, a method employing a basic amino acid (JP-A-59-106413), a method employing a guanidium salt (JP-A-11-180837) and a method employing a carbonate (JP-B-7-59490) are well known.

However, any of these methods has an insufficient decolorizing performance and can not be successful in dying the hairs a light color tone, although it can overcome the problems associated with the irritative odor. It also has an insufficient dying performance, and suffers from a difficulty in dying the hairs a deep color, to which a solution has been desired.

SUMMARY OF THE INVENTION

Accordingly, an objective of the invention is to provide a hair dye composition having sufficient decolorizing performance and dying performance without exhibiting any irritative odor, and also having an ability of imparting the hairs with an excellent smoothness.

As a result of eager study to achieve the objective, we have found that, by employing a combination of a higher alcohol and a quaternary ammonium salt cationic surfactant in a certain ratio, it becomes possible to increase the decolorizing performance and the dying performance and also to substitute the ammonia as an alkaline agent with an alkanolamine having a less irritative odor, whereby we have established the invention.

Thus, the aspect of the invention is a hair dye composition comprising:
a first agent containing an alkanolamine and an oxidation dye; and,
a second agent containing an oxidant,
wherein a higher alcohol and a quaternary ammonium salt cationic surfactant are contained in the first agent and/or the second agent;
wherein the molar ratio of the higher alcohol to the quaternary ammonium salt cationic surfactant is in the range of 3 to 15.

In the composition described above, it is preferable that substantially no ammonia is contained.

In the composition described above, it is preferable that two or more kinds of higher alcohols are contained. By containing two or more kinds of higher alcohols, the stability of a first agent over a prolonged period at a low temperature becomes satisfactory.

In the composition described above, it is also preferable that a polyoxyethylene alkyl ether nonionic surfactant are further contained in the first agent and/or the second agent;
wherein the weight of the polyoxyethylene alkyl ether nonionic surfactant incorporated in each of the first agent and the second agent is less than the weight of the quaternary ammonium salt cationic surfactant incorporated. By incorporating the polyoxyethylene alkyl ether nonionic surfactant and the quaternary ammonium salt cationic surfactant in the quantities specified above, an excellent stability of a first agent and a second agent over a prolonged period can be achieved, and excellent smoothness and gloss can be imparted to the hairs without developing any sticky touch.

In the composition described above, it is preferable that the quaternary ammonium salt cationic surfactant is contained in an amount of 0.05 to 5.0% by weight based on the entire composition.

In the composition described above, it is also preferable that an amino-modified polymer silicone or ammonium-modified polymer silicone represented by Formula (I) is contained in the first agent and/or the second agent. By further incorporating the amino-modified polymer silicone or ammonium-modified polymer silicone, the dying performance is further promoted, and a smoother touch of the finish can be achieved.

(Formula I)

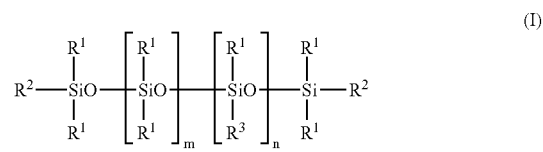

wherein $R^1$ is a methyl group or partly a phenyl group, $R^2$ is the same as $R^3$ or a methyl group or a hydroxyl group, $R^3$ is an amino group- or ammonium group-containing substituent represented by Formula $R^4Z$ wherein $R^4$ is a divalent alkylene group having 3 to 6 carbon atoms, Z is a monovalent group selected from the group consisting of $-NR^5_2$, $-N^+R^5_3A$, $-NR^5(CH_2)_aNR^5_2$, $-NR^5(CH_2)_aN^+R^5_3A$ and $-NR^5(CH_2)_aN(R^5)C=O(R^6)$ wherein $R^5$ is hydrogen or an alkyl group having 1 to 4 carbon atoms, $R^6$ is an alkyl group having 1 to 4 carbon atoms, A is Cl, Br or I, and a is an integer of 2 to 6, and each of m and n is a positive integer and m+n is an integer of 3000 to 20000, and n/m is $1/500$ to $1/10000$.

As used herein, the expression "containing substantially no ammonia" means that the ammonia is not an essential component and sufficient decolorizing performance and dying performance are obtained without the ammonia but the ammonia may be contained to an extent causing no irritative odor. Thus, while an ammonia-containing hair dye composition which exhibits an irritative odor or undergoes a reduction in the decolorizing performance or dying performance when the ammonia is removed from it is not encompassed by the invention, an ammonia-containing composition whose decolorizing performance or dying performance is not affected adversely even when the ammonia is removed from it is encompassed by the invention.

DETAILED DESCRIPTION OF THE PREFERRED EMBODIMENT

Figure 1:
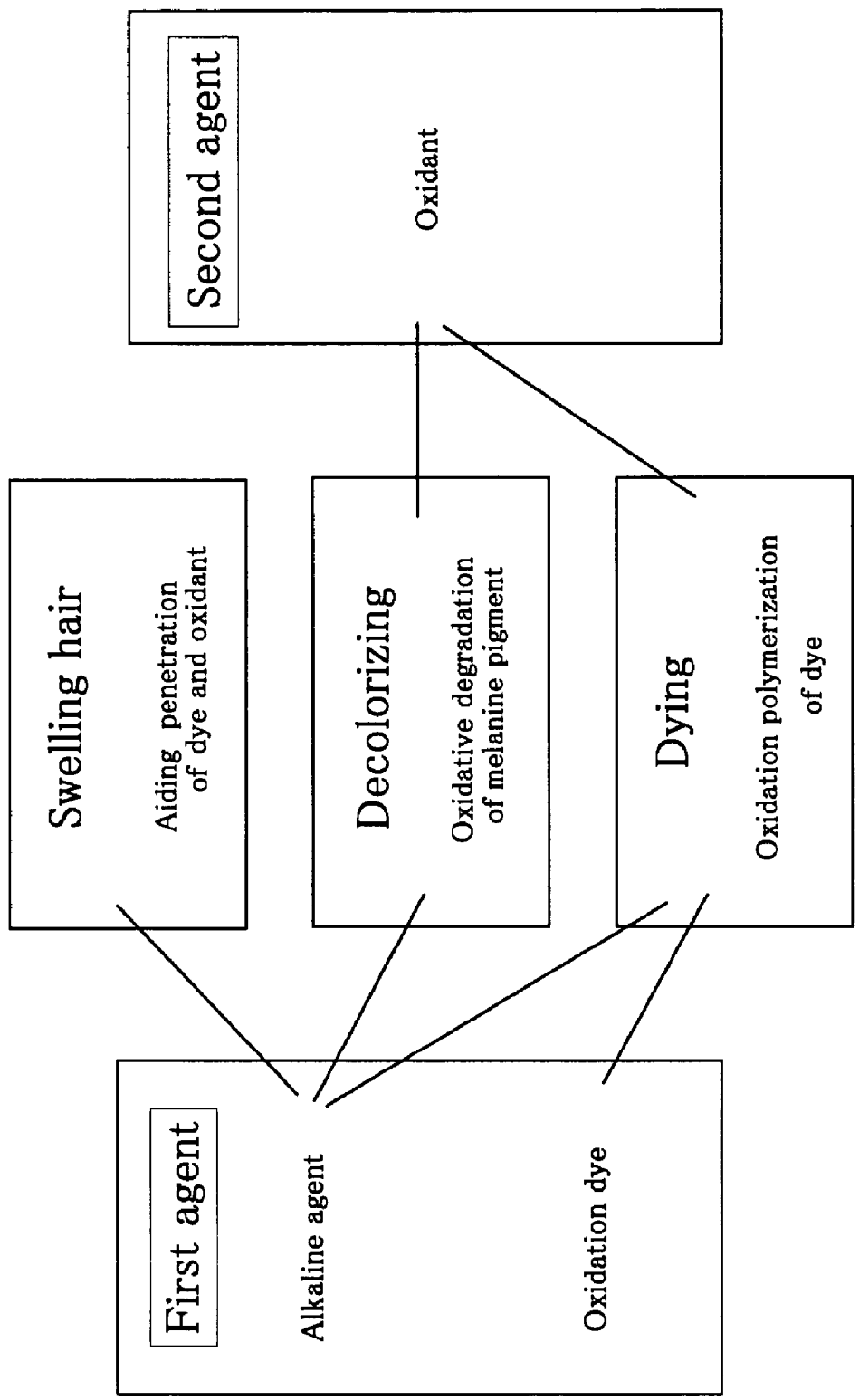
FIG. 1 shows a schematic view of the mechanism of a hair dye.

In the following section, the preferred embodiment for carrying out the present invention will be explained in detail.

<Higher Alcohol>

While the higher alcohol employed in a hair dye composition according to the invention is not limited particularly as long as it is employed usually in a cosmetic product, it may for example be lauryl alcohol, myristyl alcohol, cetyl alcohol, cetanol, stearyl alcohol, cetostearyl alcohol, behenyl alcohol, 2-octyldodecanol and oleyl alcohol, which may be employed alone or in combination of two or more.

Those preferred especially are cetyl alcohol, cetanol, stearyl alcohol, cetostearyl alcohol, behenyl alcohol and oleyl alcohol.

A higher alcohol may be incorporated into either the first agent or the second agent, or into both.

<Quaternary Ammonium Salt Cationic Surfactant>

While the quaternary ammonium salt cationic surfactant employed in a hair dye composition according to the invention is not limited particularly as long as it is employed usually in a cosmetic product, it may for example be a monoalkyl quaternary ammonium salt represented by Formula (II):

(Formula II)

wherein $R^7$ is a straight or branched alkyl group having 8 to 36 carbon atoms which may be substituted by a hydroxyl group, $R^8$, $R^9$ and $R^{10}$ are same or different, and each is an alkyl group having 1 to 3 carbon atoms or benzyl group which may be substituted by a hydroxyl group, and X is a halogen atom or an alkyl sulfate group having 1 to 2 carbon atoms, or a dialkyl quaternary ammonium salt represented by Formula (III):

(Formula III)

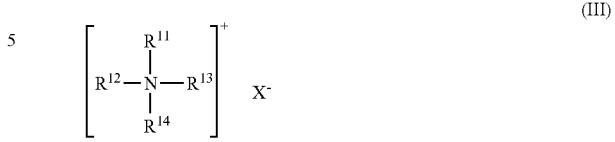

wherein $R^{11}$ and $R^{12}$ are same or different and each is a straight or branched alkyl group having 8 to 36 carbon atoms which may be substituted by a hydroxyl group, $R^{13}$ and $R^{14}$ are same or different, and each is an alkyl group having 1 to 3 carbon atoms or benzyl group which may be substituted by a hydroxyl group, and X is a halogen atom or an alkyl sulfate group having 1 to 2 carbon atoms.

A monoalkyl quaternary ammonium salt represented by Formula (II) shown above may for example be lauryltrimethylammonium chloride, lauryltrimethylammonium bromide, myristyltrimethylammonium chloride, myristyltrimethylammonium bromide, cetyltrimethylammonium chloride, cetyltrimethylammonium bromide, stearyltrimethylammonium chloride, stearyltrimethylammonium bromide, behenyltrimethylammonium chloride, behenyltrimethylammonium bromide, cetyltrimethylammonium methanesulfonate, stearyltrimethylammonium methanesulfonate, myristyldimethylbenzylammonium chloride, cetyldimethylbenzylammonium chloride, stearyldimethylbenzylammonium chloride, octyldihydroxyethylmethylammonium chloride, 2-decyltetradecyltrimethylammonium chloride, 2-dodecylhexadecyltrimethylammonium chloride and the like.

A dialkyl quaternary ammonium salt represented by Formula (III) shown above may for example be distearyldimethylammonium chloride, dicetyldimethylammonium chloride, dicocoyldimethylammonium chloride, dialkyl ($C_{12}$–$C_{15}$)dimethylammonium chloride, dialkyl($C_{14}$–$C_{18}$) dimethylammonium chloride, di(2-hexyldecyl) dimethylammonium chloride, di(2-oxtyldodecyl) dimethylammonium chloride and the like.

Among the quaternary ammonium salt cationic surfactants described above, stearyltrimethylammonium chloride and behenyltrimethylammonium chloride are preferred especially since a satisfactorily stable composition can readily be obtained.

A quaternary ammonium salt cationic surfactant described above is contained preferably in an amount of 0.05 to 5.0% by weight based on the entire composition as a mixture of the first agent and the second agent. An amount less than 0.05% by weight may lead to a poor hair touch after dying operation, while an amount exceeding 5.0% by weight may lead to a too higher viscosity.

One or more of quaternary ammonium salt cationic surfactants may be incorporated into either the first agent or the second agent, or into both.

It is preferable that the molar ratio of a higher alcohol to a quaternary ammonium salt cationic surfactant is in the range of 3 to 15 in the entire composition as a mixture of the first agent and the second agent. A molar ratio within the range specified above gives satisfactory decolorizing performance, dying performance and hair touch after dying operation, but a molar ratio less than 3 or exceeding 15 gives insufficient decolorizing effect, insufficient dying effect and poor hair touch after dying operation.

A molar ratio between a higher alcohol and a quaternary ammonium salt cationic surfactant within the range specified above imparts a mixture of the first agent and the second agent with a thixotropic property. The thixotropic property is a behavior of a gel which is converted into a fluidized sol as a result of stirring but becomes the gel again after being allowed to stand, and exhibits a hysteresis in the curve of the coefficient of viscosity vs shear force. Thus, the mixture is less viscose and readily applied and spread over the hairs (sol), and once applied it remains on the hair without running down easily (gel). A molar ratio less than 3 gives a too high viscosity which leads to a difficulty in applying and spreading the composition, while a ratio exceeding 15 gives a too low viscosity which allows the composition after application to run down easily.

Although a relatively higher molar ratio (8 or higher) may leads to a poor stability of a first agent and a second agent over a prolonged period at a low temperature even when the molar ratio is still within the range specified above, the incorporation of two or more kinds of higher alcohols makes the stability over a prolonged period at a low temperature satisfactory. Thus, when only a single higher alcohol is present in a system whose molar ratio is 8 or higher, the α crystal structure is readily converted into the β crystal structure or the γ crystal structure, allowing the composition to exhibit an undesirable luster. On the contrary, the incorporation of two or more kinds of higher alcohols enables a reduction in the crystal transfer temperature, allowing the α crystal structure to be maintained easily. For example, when using a combination of cetyl alcohol and stearyl alcohol, the weight ratio of cetyl alcohol and stearyl alcohol is preferably within the range from 8:2 to 4:6.

<Polyoxyethylene Alkyl Ether Nonionic Surfactant>

While a first and a second agent of the invention can readily be imparted with a satisfactory stability when using stearyltrimethylammonium chloride, behenyltrimethylammonium chloride among the quaternary ammonium salt cationic surfactants described above, the stability over a prolonged period of the both of the first and second agents may become poor as a result of the effects of an alkaline agent, oxidant or oxidation dye. Accordingly, the stability over a prolonged period can be improved by adding a polyoxyethylene alkyl ether nonionic surfactant.

A polyoxyethylene alkyl ether nonionic surfactant employed in an inventive hair dye composition may for example be POE cetyl ether, POE isostearyl ether, POE lauryl ether, POE oleyl ether, POE stearyl ether, POE behenyl ether, POE 2-octyldodecyl ether and POE cholestanol ether. One or more of the polyoxyethylene alkyl ether nonionic surfactant may be incorporated into either the first agent or the second agent, or into both.

By incorporating a polyoxyethylene alkyl ether nonionic surfactant, the stability over a prolonged period of first agent and second agent is improved, but the incorporation of a large amount may lead to a poor hair touch after dying operation.

Accordingly, in each of the first and second agents, the weight of the polyoxyethylene alkyl ether nonionic surfactant to be incorporated is preferably less than the weight of the quaternary ammonium salt cationic surfactant incorporated. As a result of the incorporation in the amounts specified above, the excellent stability over a prolonged period can be obtained, and the hairs can be imparted with excellent smoothness and gloss without exhibiting any sticky touch.

<Amino-modified Polymer Silicone and Ammonium-modified Polymer Silicone>

A hair dye composition of the invention can be imparted further with an increased dying performance and an ability of giving a smoother finish touch by incorporating an amino-modified polymer silicone or ammonium-modified polymer silicone represented by Formula (I):

(Formula I)

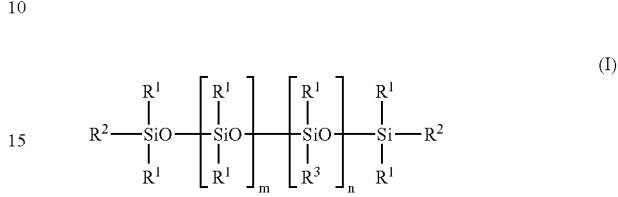

wherein $R^1$ is a methyl group or partly a phenyl group, $R^2$ is the same as $R^3$ or a methyl group or a hydroxyl group, $R^3$ is an amino group- or ammonium group-containing substituent represented by Formula $R^4Z$ wherein $R^4$ is a divalent alkylene group having 3 to 6 carbon atoms, Z is a monovalent group selected from the group consisting of $—NR^5{}_2$, $—N^+R^5{}_3A$, $—NR^5(CH_2)_aNR^5{}_2$, $—NR^5(CH_2)_aN^+R^5{}_3A$ and $—NR^5(CH_2)_aN(R^5)C=O(R^6)$ wherein $R^5$ is hydrogen or an alkyl group having 1 to 4 carbon atoms, $R^6$ is an alkyl group having 1 to 4 carbon atoms, A is Cl, Br or I, and a is an integer of 2 to 6, and each of m and n is a positive integer and m+n is an integer of 3000 to 20000, and n/m is 1/500 to 1/10000.

Those employed preferably are the compound represented by Formula (I) wherein $R^1$ is a methyl group, $R^2$ is a methyl group or hydroxyl group, $R^3$ is $—(CH_2)_3NH_2$, $—(CH_2)_3N(CH_3)_2$ and $—(CH_2)_3N^+(CH_3)_3Cl^-$.

While the value of m+n in Formula (I) is 3000 to 20000, it is preferable to be 4000 to 20000. A value of m+n less than 3000 results in a oily composition and an insufficient ability of increasing the dying performance. On the other hand, a value exceeding 20000 results in a difficulty in dissolving in other components. While the value of n/m is 1/500 to 1/10000, it is preferable to be 1/500 to 1/2000. A value of n/m exceeding 1/500 leads to an increased amino group or ammonium group content in a polymer silicone, which may lead to a crosslinking reaction during the manufacturing processes and which is not also desirable in view of a problematic odor of the starting materials. On the other hand, a value less than 1/10000 results in an insufficient ability of increasing the dying performance.

An amino-modified or ammonium-modified polymer silicone employed in the invention can be produced by a standard method. For example, it can be produced by subjecting γ-aminopropylmethyldiethoxysilane, cyclic dimethylpolysiloxane, hexamethyldisiloxane to a condensation polymerization in the presence of an alkaline catalyst, to which the methods are not limited.

The amount of an amino-modified or ammonium-modified polymer silicone to be incorporated is 0.01 to 10.0% by weight, preferably 0.1 to 7.0% by weight in the composition. An amount less than 0.01% by weight can not give an ability of increasing the dying performance, while an amount exceeding 10.0% by weight may give a sticky touch on the hair. One or more of amino-modified or ammonium-modified polymer silicone may be incorporated into either the first agent or the second agent, or into both.

<Alkaline Agent>

In a hair dye composition, an alkaline agent is contained in the first agent and plays an important role. Thus, the alkaline agent makes the system alkaline to allow the hairs to be soften, swollen and dyed easily, and it also decomposes oxidants such as hydrogen peroxide which is an active component in the second agent upon mixing the first and second agents to generate perhydroxyanion, which decomposes melanin pigments in the hairs, whereby decolorizing the hair. It also has an ability of oxidizing and fixing an oxidation dye in the hairs as its basic effect.

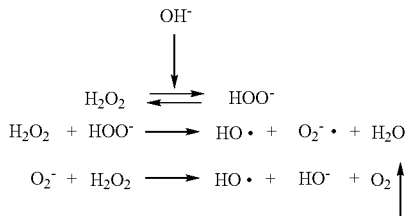

As an alkaline agent contained usually in a hair dye composition, ammonia is employed frequently. However, the use of ammonia poses a serious problem experience as a marked irritative odor.

In the invention, the incorporation of a higher alcohol and a quaternary ammonium salt cationic surfactant in amounts specified above leads to a significant improvement in the decolorizing performance and the dying performance, because of which the ammonia can be replaced with an alkanolamine having a less irritative odor, whereby overcoming the problems of the irritative odor.

An alkanolamine in a hair dye composition of the invention may for example be monoethanolamine, diethanolamine, triethanolamine, monopropanol amine, dipropanol amine, tripropanol amine, 2-amino-2-methyl-1,3-propanediol, 2-amino-2-methyl-1-propanol, 2-amino-2-hydroxymethyl-1,3-propanediol and the like, which may be employed alone or in combination of two or more.

Those preferred especially are monoethanolamine, monopropanol amine and 2-amino-2-methyl-1-propanol.

An alkanolamine is contained preferably in an amount of 0.1 to 10% by weight, especially 0.5 to 5% by weight based on the entire composition as a mixture of the first agent and the second agent.

An amount less than 0.1% by weight may lead to an insufficient decolorizing performance or dying performance. An amount exceeding 10% by weight does not allow a corresponding increase in the effect to be expected, and may exhibit a problematic skin irritation.

While the invention gives sufficient decolorizing performance and dying performance even without ammonia, it may contain the ammonia as long as the irritative odor is negligible. It is preferable to use the ammonia in an amount less than 0.1% by weight based on the entire composition as a mixture of the first agent and the second agent.

<Oxidation Dye>

An oxidation dye as developer incorporated into the first agent of a hair dye composition of the invention may for example be p-phenylenediamines each having one or more $NH_2$-groups, $NHR$-group or $NHR_2$-group (wherein R is an alkyl group or hydroxyalkyl group having 1 to 4 carbon atoms) such as p-phenylenediamine, p-toluylenediamine, N-methyl-p-phenylenediamine, N,N-dimethyl-p-phenylendiamine, N,N-diethyl-2-methyl-p-phenylenediamine, N-ethyl-N-(hydroxyethyl)-p-phenylenediamine, chloro-p-phenylenediamine, 2-(2'-hydroxyethylamino)5-aminotouene, N,N-bis-(2-hydroxyethyl)-p-phenylenediamine, methoxy-p-phenylenediamine, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine, N-2-methoxyethyl-p-phenylenediamine; 2,5-diaminopyridine derivative; p-aminophenols, o-aminophenols and o-phenylenediamines such as p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol,2,4-diaminophenol, 5-aminosalicylic acid.

A coupler may also be added such as α-naphthol, o-cresol, m-cresol, 2,6-dimethyl phenol, 2,5-dimethyl phenol, 3,4-dimethyl phenol, 3,5-dimethyl phenol, benzenecatechin, pyrogallol, 1,5-dihydroxynaphthalene, 1,7-dihydroxynaphthalene, 5-amino-2-methyl phenol, 5-(2'-hydroxyethylamino)-4-methoxy phenol, hydroquinone, 2,4-diaminoanisole, m-toluylenediamine, 4-aminophenol, resorcin, resorcin monomethyl ether, m-phenylenediamine, 1-phenyl-3-methyl-5-pyrazolone, 1-phenyl-3-amino-5-pyrazolone, 1-phenyl-3,5-diketo-pyrazolidine, 1-methyl-7-dimethylamino-4-hydroxy-2-quinolone, m-aminophenol, 4-chlororesorcin, 2-methyl resorcin, 2,4-diamino phenoxyethanol, 2,6-diaminopyridine, 3,5-diaminotrifluoromethylbenzene, 2,4-diamino fluorobenzene, 3,5-diamino fluorobenzene, 2,4-diamino-6-hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine.

In addition to the substances listed above, substances described in "Quasi-drug standard" (YAKUJINIPPO, published in June, 1991) can be employed as appropriate. It is also possible to incorporate acidic dyes, basic dyes, HC dyes.

In the invention, the incorporation of a higher alcohol and a quaternary ammonium salt cationic surfactant in amounts specified above leads to a significant improvement in the decolorizing performance and the dying performance, because of which the amount of the dyes to be incorporated can be reduced when compared with a conventional product.

<Oxidizing Agent>

An oxidant employed in the second agent of a hair dye composition of the invention may for example be hydrogen peroxide, sodium percarbonate, sodium sulfate hydrogen peroxide adduct, sodium pyrophoshate hydrogen peroxide adduct. The oxidant may be contained preferably in an amount of 0.1 to 20% by weight, especially 1 to 10% by weight based on the entire composition as a mixture of the first agent and the second agent.

While an inventive hair dye composition may be used by mixing the first agent and the second agent in any ratio, the weight ratio of the first agent to the second agent is preferably 2:1 to 1:3.

In a composition according to the invention, the essential components described above may be combined with any known base components depending on their desirable formulations or dosage forms, as long as no adverse quantitative or qualitative influence is exerted on the effect of the invention by such a combination. For example, it may contain, in addition to the components described above, one or more of lipid fractions, pH modifier, moistening agent, polypeptides, glycols, alcohols, organic solvents, particulates, antioxidants, preservatives, metal sequestering agents, protein derivatives, amino acids, conditioners, silicones, plant extracts, vitamins, colorants, fragrances, pigments, UV absorbers and the like.

An inventive dye composition can be produced by a standard method as any of the formulations such as a clear liquid, emulsion, cream, gel, paste, aerosol, aerosol foam and the like. The morphology of the first agent is not necessarily identical to that of the second agent, and the first agent as a cream and the second agent as an emulsion may be combined.

When an inventive hair dye composition contains no dye, it can be used also as a decolorizing composition. This decolorizing composition can adjust the color of the hairs at a light color without exerting substantial damage on the hair while giving a smooth touch of the hairs after decolorizing operation. In addition, a particulate oxidant may be added to the decolorizing composition to promote the decolorizing effect. Such a particulate oxidant may for example be potassium persulfate, sodium persulfate, ammonium persulfate, potassium percarbonate, sodium percarbonate and the like.

Preferred examples of the invention is further detailed below. The invention is not limited by the examples. Unless otherwise stated, an amount incorporated (%) is a % by weight.

First, typical methods for evaluating the performance (decolorizing performance, dying performance, application performance, hair touch, stability over time and irritative odor) of a hair dye composition according to the invention and the evaluation criteria are described below.

Evaluation Methods and Criteria of Performance

<Decolorizing Performance>

In the decolorizing ability test, an example from which a dye (paraphenylenediamine, resorcine, p-nitromethaphenylenediamine, Orange II, HC Red BN) was removed was evaluated.

The first agent and the second agent were mixed in the weight ratio of 1:1 and 8 g of the resultant mixture was applied onto 4 g of a black hair bundle (human hair), allowed to stand at 30° C. for 20 minutes, rinsed thoroughly with warm water, shampooed, and then dried with a gentle air, and then subjected to the evaluation of the decolorizing degree.

The lightness was indicated as a tone, and a lighter color was designated by a smaller value, with tone 5 being assigned to an ordinary black hair and tone 1 being assigned to a highly-bleached hair. The hair was judged to be decolorized (become lighter) usually when the tone becomes less than 4. Accordingly, the decolorizing degree was evaluated visually in accordance with the criteria shown below.

A: Less than tone 3 (became very light)
B: Tone 3 or higher and less than tone 4 (became lighter)
C: Tone 4 or higher (not became lighter)

<Dying Performance>

The first agent and the second agent were mixed in the weight ratio of 1:1 and 8 g of the resultant mixture was applied onto 4 g of a goat hair bundle, allowed to stand at 30° C. for 20 minutes, rinsed thoroughly with warm water, shampooed, and then dried with a gentle air, and then examined visually for the dying degree in accordance with the following evaluation criteria.

AA: Dyed to deep brown
A: Dyed to brown
B: Dyed to pale blown
C: Almost not dyed <Application Performance>

The application performance of a composition (spreading performance, resistance to dropping out) was evaluated organoleptically by 10 panelists in accordance with the following criteria.

A: 8 or more panelists answered "easily applied"
B: 4 to 7 panelists answered "easily applied"
C: 3 or less panelists answered "easily applied"

<Hair Touch>

The tough of the hairs after being dyed (whether it is smooth and moist without exhibiting any sticky touch) was evaluated organoleptically by 10 panelists in accordance with the following criteria.

AA: 9 or more panelists answered "good touch"
A: 6 to 8 panelists answered "good touch"
B: 4 to 6 panelists answered "good touch"
C: 3 or less panelists answered "good touch"

<Temporal Stability>

Each of the first agent and the second agent was filled in a glass bottle, allowed to stand at 0° C., room temperature and 50° C. for 1 month, and then evaluated in accordance with the following criteria.

A: No separation
B: Slight separation of oily fractions
C: Marked separation of oily fractions <Irritative Odor>

The first agent and the second agent were mixed in the weight ratio of 1:1 and the resultant mixture was examined for the irritative odor in accordance with the following evaluation criteria.

A: No irritative odor
B: Slight irritative odor
C: Intense irritative odor

[Molar Ratio of Higher Alcohol to Quaternary Ammonium Salt Cationic Surfactant]

The relationship between the molar ratio of the higher alcohol to the quaternary ammonium salt cationic surfactant and the performance was investigated. The results are shown in Tables 1 and 2.

The molecular weights are shown below.
Cetyl alcohol: 242.4
Stearyl alcohol: 270.5
Oleyl alcohol: 268.5
Behenyltrimethylammonium chloride: 404.2
Stearyltrimethylammonium chloride: 348.1
Distearldimethylammonium chloride: 586.5

TABLE 1

| | Example | | | | |
|---|---|---|---|---|---|
| | 1 | 2 | 3 | 4 | 5 |
| Higher alcohol/Quaternary ammonium salt cationic surfactant (molar ratio) | 19.88 | 13.91 | 6.96 | 3.48 | 1.16 |
| First agent (Cream state) Quaternary ammonium salt cationic surfactant | | | | | |
| Stearyltrimethylammonium chloride | 0.7 | 1.0 | 2.0 | 4.0 | 12.0 |
| Higher alcohol | | | | | |
| Cetyl alcohol | 7.0 | 7.0 | 7.0 | 7.0 | 7.0 |
| Stearyl alcohol | 3.0 | 3.0 | 3.0 | 3.0 | 3.0 |

TABLE 1-continued

|  | Example | | | | |
|---|---|---|---|---|---|
|  | 1 | 2 | 3 | 4 | 5 |
| Alkaline agent | | | | | |
| Monoethanolamine | 5.0 | 5.0 | 5.0 | 5.0 | 5.0 |
| Polyoxyethylene alkyl ether nonionic surfactant | | | | | |
| POE(20)cetyl ether | 0.2 | 0.2 | 0.2 | 0.2 | 0.2 |
| Propylene glycol | 5.0 | 5.0 | 5.0 | 5.0 | 5.0 |
| Sodium dithionite | 0.1 | 0.1 | 0.1 | 0.1 | 0.1 |
| Disodium edentate dehydrate | 0.2 | 0.2 | 0.2 | 0.2 | 0.2 |
| Paraphenylendiamine | 1.0 | 1.0 | 1.0 | 1.0 | 1.0 |
| Resorcin | 0.5 | 0.5 | 0.5 | 0.5 | 0.5 |
| Paranitromethaphenylenediamine | 0.1 | 0.1 | 0.1 | 0.1 | 0.1 |
| Purified water | Remainder | | | | |
| Second agent (liquid state) | | | | | |
| Hydrogen peroxide water (31%) | 16.0 | 16.0 | 16.0 | 16.0 | 16.0 |
| Methylparaben | 0.1 | 0.1 | 0.1 | 0.1 | 0.1 |
| Phosphoric acid | 0.2 | 0.2 | 0.2 | 0.2 | 0.2 |
| Disodium hydrogenphosphate | 0.2 | 0.2 | 0.2 | 0.2 | 0.2 |
| Purified water | Remainder | | | | |
| Decolorizing performance | C | A | A | A | B |
| Dying performance | C | A | A | A | B |
| Application performance | B | A | A | A | C |
| Hair touch | B | A | A | A | B |
| Temporal stability | A | A | A | A | B |
| Irritative odor | A | A | A | A | A |

TABLE 2

|  | Example | | | |
|---|---|---|---|---|
|  | 6 | 7 | 8 | 9 |
| Higher alcohol/Quaternary ammonium salt cationic surfactant (molar ratio) | 6.96 | 8.08 | 11.72 | 12.96 |
| First agent (Cream state) | | | | |
| Quaternary ammonium salt cationic surfactant | | | | |
| Behenyltrimethylammonium chloride | — | 2.0 | — | — |
| Stearyltrimethylammonium chloride | 1.0 | — | — | 1.0 |
| Distearyldimethylammonium chloride | — | — | 2.0 | — |
| Higher alcohol | | | | |
| Cetyl alcohol | 3.5 | 7.0 | 7.0 | — |
| Stearyl alcohol | 1.5 | 3.0 | 3.0 | — |
| Oleyl alcohol | — | — | — | 10.0 |
| Alkaline agent | | | | |
| Monoethanolamine | 5.0 | 5.0 | 5.0 | 5.0 |
| Polyoxyethylene alkyl ether nonionic surfactant | | | | |
| POE(20) cetyl ether | 0.2 | — | — | — |
| POE(4) oleyl alcohol ether | — | 0.2 | 0.2 | 0.2 |
| Propylene glycol | 5.0 | 5.0 | 5.0 | 5.0 |
| Sodium dithionite | 0.1 | 0.1 | 0.1 | 0.1 |
| Disodium edentate dehydrate | 0.2 | 0.2 | 0.2 | 0.2 |
| Paraphenylendiamine | 1.0 | 1.0 | 1.0 | 1.0 |
| Resorcin | 0.5 | 0.5 | 0.5 | 0.5 |
| Paranitromethaphenylenediamine | 0.1 | 0.1 | 0.1 | 0.1 |
| Purified water | Remainder | | | |
| Second agent (Liquid state) | | | | |
| Hydrogen peroxide water (31%) | 16.0 | 16.0 | 16.0 | 16.0 |
| Methylparaben | 0.1 | 0.1 | 0.1 | 0.1 |
| Phosphoric acid | 0.2 | 0.2 | 0.2 | 0.2 |
| Disodium hydrogenphosphate | 0.2 | 0.2 | 0.2 | 0.2 |
| Purified water | Remainder | | | |
| Decolorizing performance | A | A | A | A |
| Dying performance | A | A | A | A |

TABLE 2-continued

|  | Example | | | |
|---|---|---|---|---|
|  | 6 | 7 | 8 | 9 |
| Application performance | A | A | A | A |
| Hair touch | A | A | A | A |
| Temporal stability | A | A | A | B |
| Irritative odor | A | A | A | A |

The Example 1 whose molar ratio of the higher alcohol to the quaternary ammonium salt cationic surfactant was 15 or higher and the Example 5 whose molar ratio was less than 3 resulted in inferior decolorizing and dying effects on the hair and a poor hair touch. In addition, the Example 1 whose molar ratio was 15 or higher resulted in a viscosity which was so low as to cause running down of the composition after the application, while the Example 3 whose molar ratio was less than 3 resulted in a viscosity which was so high that spreading the composition was difficult. On the contrary, any of the Examples 2 to 4, 6 to 9 which are the hair dye compositions according to the invention exhibited an excellent performance, since it had a molar ratio of 3 to 15. Nevertheless, the Example 9 whose molar ratio was 8 or higher and contained only a single higher alcohol exhibited a luster.

[Amount of Quaternary Ammonium Salt Cationic Surfactant]

The relationship between the amount of the quaternary ammonium salt cationic surfactant and the performance was investigated. The results are shown in Table 3.

TABLE 3

|  | Example | | | | |
|---|---|---|---|---|---|
|  | 10 | 11 | 12 | 13 | 14 |
| Blending Quantity of Quaternary ammonium salt cationic surfactant by weight based on the entire composition | 0.025 | 0.05 | 0.25 | 5.0 | 6.0 |
| First agent (Cream state) | | | | | |
| Quaternary ammonium salt cationic surfactant | | | | | |
| Stearyltrimethylammonium chloride | 0.05 | 0.1 | 0.5 | 10.0 | 12.0 |
| Higher alcohol | | | | | |
| Cetyl alcohol | 0.18 | 0.36 | 1.8 | 21.0 | 7.0 |
| Stearyl alcohol | 0.08 | 0.18 | 0.8 | 9.0 | 3.0 |
| Alkaline agent | | | | | |
| Monoethanolamine | 5.0 | 5.0 | 5.0 | 5.0 | 5.0 |
| Polyoxyethylene alkyl ether nonionic surfactant | | | | | |
| POE(20) cetyl ether | 0.2 | 0.2 | 0.2 | 0.2 | 0.2 |
| Propylene glycol | 5.0 | 5.0 | 5.0 | 5.0 | 5.0 |
| Sodium dithionite | 0.1 | 0.1 | 0.1 | 0.1 | 0.1 |
| Disodium edentate dehydrate | 0.2 | 0.2 | 0.2 | 0.2 | 0.2 |
| Paraphenylendiamine | 1.0 | 1.0 | 1.0 | 1.0 | 1.0 |
| Resorcin | 0.5 | 0.5 | 0.5 | 0.5 | 0.5 |
| Paranitromethaphenylenediamine | 0.1 | 0.1 | 0.1 | 0.1 | 0.1 |
| Purified water | Remainder | | | | |
| Second agent (Liquid state) | | | | | |
| Hydrogen peroxide water (31%) | 16.0 | 16.0 | 16.0 | 16.0 | 16.0 |
| Methylparaben | 0.1 | 0.1 | 0.1 | 0.1 | 0.1 |
| Phosphoric acid | 0.2 | 0.2 | 0.2 | 0.2 | 0.2 |
| Disodium hydrogenphosphate | 0.2 | 0.2 | 0.2 | 0.2 | 0.2 |
| Purified water | Remainder | | | | |

TABLE 3-continued

|  | Example | | | | |
|---|---|---|---|---|---|
|  | 10 | 11 | 12 | 13 | 14 |
| Decolorizing performance | C | A | A | A | B |
| Dying performance | B | A | A | A | B |
| Application performance | B | A | A | A | C |
| Hair touch | C | A | A | A | B |
| Temporal stability | A | A | A | A | B |
| Irritative odor | A | A | A | A | A |

The Example 10 in which the amount of the quaternary ammonium salt cationic surfactant was less than 0.05% by weight based on the entire composition exhibited a poor hair touch. In addition, it was running down upon application, and exhibited poor decolorizing and dying effects. The Example 14 containing more than 5.0% by weight resulted in a difficulty in spreading upon application and inferiorities in decolorizing and dying effects, hair touch, and stability over a prolonged period. On the contrary, any of the Examples 11 to 13 which are the hair dye compositions according to the invention exhibited an excellent performance, since it contains the quaternary ammonium salt cationic surfactant in an amount of 0.05 to 5.0% by weight.

[Type of Alkaline Agent]

The relationship between the kind of alkaline agent and the performance was investigated. The results are shown in Table 4.

TABLE 4

|  | Example | | | |
|---|---|---|---|---|
|  | 15 | 16 | 17 | 18 |
| First agent (Cream state) | | | | |
| Alkaline agent | | | | |
| Monoethanolamine | 5.0 | — | — | 5.0 |
| Monopropanolamine | — | 6.0 | — | — |
| Aqueous ammonia (28%) | — | — | 5.0 | 0.1 |
| Higher alcohol | | | | |
| Cetyl alcohol | 7.0 | 7.0 | 7.0 | 7.0 |
| Stearyl alcohol | 3.0 | 3.0 | 3.0 | 3.0 |
| Quaternary ammonium salt cationic surfactant | | | | |
| Stearyltrimethylammonium chloride | 2.0 | 2.0 | 2.0 | 2.0 |
| Polyoxyethylene alkyl ether nonionic surfactant | | | | |
| POE(20) cetyl ether | 0.2 | — | 0.2 | — |
| POE(4) oleyl ether | — | 0.2 | — | 0.2 |
| Propylene glycol | 5.0 | 5.0 | 5.0 | 5.0 |
| Sodium dithionite | 0.1 | 0.1 | 0.1 | 0.1 |
| Disodium edentate dehydrate | 0.2 | 0.2 | 0.2 | 0.2 |
| Paraphenylendiamine | 1.0 | 1.0 | 1.0 | 1.0 |
| Resorcin | 0.5 | 0.5 | 0.5 | 0.5 |
| Paranitromethaphenylenediamine | 0.1 | 0.1 | 0.1 | 0.1 |
| Purified water | Remainder | | | |
| Second agent (Liquid state) | | | | |
| Hydrogen peroxide water (31%) | 16.0 | 16.0 | 16.0 | 16.0 |
| Methylparaben | 0.1 | 0.1 | 0.1 | 0.1 |
| Phosphoric acid | 0.2 | 0.2 | 0.2 | 0.2 |
| Disodium hydrogenphosphate | 0.2 | 0.2 | 0.2 | 0.2 |
| Purified water | Remainder | | | |
| Decolorizing performance | A | A | A | A |
| Dying performance | A | A | A | A |

TABLE 4-continued

|  | Example | | | |
|---|---|---|---|---|
|  | 15 | 16 | 17 | 18 |
| Application performance | A | A | A | A |
| Hair touch | A | A | A | A |
| Temporal stability | A | A | A | A |
| Irritative odor | A | A | C | A |

The Example 17 containing a large amount of ammonia as an alkaline agent exhibited an intense irritative odor and posed a discomfort. On the contrary, the Examples 15 and 16 each containing an alkanolamine as an alkaline agent exhibited no irritative odor. The Example 18 which contained a trace amount of ammonia also exhibited no irritative odor. The Examples 15 to 17 were excellent also in terms of the decolorizing performance and the dying performance.

Based on the results described above, each of the hair dye compositions of the invention containing an alkanolamine as an alkaline agent was proven to be excellent in terms of the decolorizing performance and the dying performance without exhibiting irritative odor.

The inventive hair dye composition can contain ammonia in such a trace amount that no irritative odor is noted.

[Weight of Quaternary Ammonium Salt Cationic Surfactant and Polyoxyethylene Alkyl Ether Nonionic Surfactant to be Incorporated]

The relationship between the weight of the quaternary ammonium salt cationic surfactant and the polyoxyethylene alkyl ether nonionic surfactant to be incorporated and the performance was investigated. The results are shown in Table 5.

TABLE 5

|  | Example | | | |
|---|---|---|---|---|
|  | 19 | 20 | 21 | 22 |
| First agent (Cream state) | | | | |
| Polyoxyethylene alkyl ether nonionic surfactant | | | | |
| POE(20) cetyl ether | — | 0.2 | 1.5 | 5.0 |
| Quaternary ammonium salt cationic surfactant | | | | |
| Stearyltrimethylammonium chloride | 2.0 | 2.0 | 2.0 | 2.0 |
| Higher alcohol | | | | |
| Cetyl alcohol | 7.0 | 7.0 | 7.0 | 7.0 |
| Stearyl alcohol | 3.0 | 3.0 | 3.0 | 3.0 |
| Alkaline agent | | | | |
| Monoethanolamine | 5.0 | 5.0 | 5.0 | 5.0 |
| Propylene glycol | 5.0 | 5.0 | 5.0 | 5.0 |
| Sodium dithionite | 0.1 | 0.1 | 0.1 | 0.1 |
| Disodium edentate dehydrate | 0.2 | 0.2 | 0.2 | 0.2 |
| Paraphenylendiamine | 1.0 | 1.0 | 1.0 | 1.0 |
| Resorcin | 0.5 | 0.5 | 0.5 | 0.5 |
| Paranitromethaphenylenediamine | 0.1 | 0.1 | 0.1 | 0.1 |
| Purified water | Remainder | | | |
| Second agent (Liquid state) | | | | |
| Hydrogen peroxide water (31%) | 16.0 | 16.0 | 16.0 | 16.0 |
| Methylparaben | 0.1 | 0.1 | 0.1 | 0.1 |
| Phosphoric acid | 0.2 | 0.2 | 0.2 | 0.2 |

TABLE 5-continued

|  | Example | | | |
|---|---|---|---|---|
|  | 19 | 20 | 21 | 22 |
| Disodium hydrogenphosphate | 0.2 | 0.2 | 0.2 | 0.2 |
| Purified water | Remainder | | | |
| Decolorizing performance | A | A | A | A |
| Dying performance | A | A | A | A |
| Application performance | A | A | A | A |
| Hair touch | A | A | A | C |
| Temporal stability | B | A | A | A |
| Irritative odor | A | A | A | A |

The Example 22 in which the weight of the polyoxyethylene alkyl ether nonionic surfactant was larger than that of the quaternary ammonium salt cationic surfactant exhibited a poor hair touch. The Example 19 into which no polyoxyethylene alkyl ether nonionic surfactant was incorporated exhibited a slightly poor stability over a prolonged period. On the contrary, any of the Examples 20 and 21 which are the hair dye compositions according to the invention exhibited an excellent stability over a prolonged period and gave an extremely smooth hair touch, since it contained the polyoxyethylene alkyl ether nonionic surfactant and also since the weight of the polyoxyethylene alkyl ether nonionic surfactant incorporated was less than the weight of the quaternary ammonium salt cationic surfactant incorporated.

[Amino-modified or Ammonium-modified Polymer Silicone]

Figure 2:
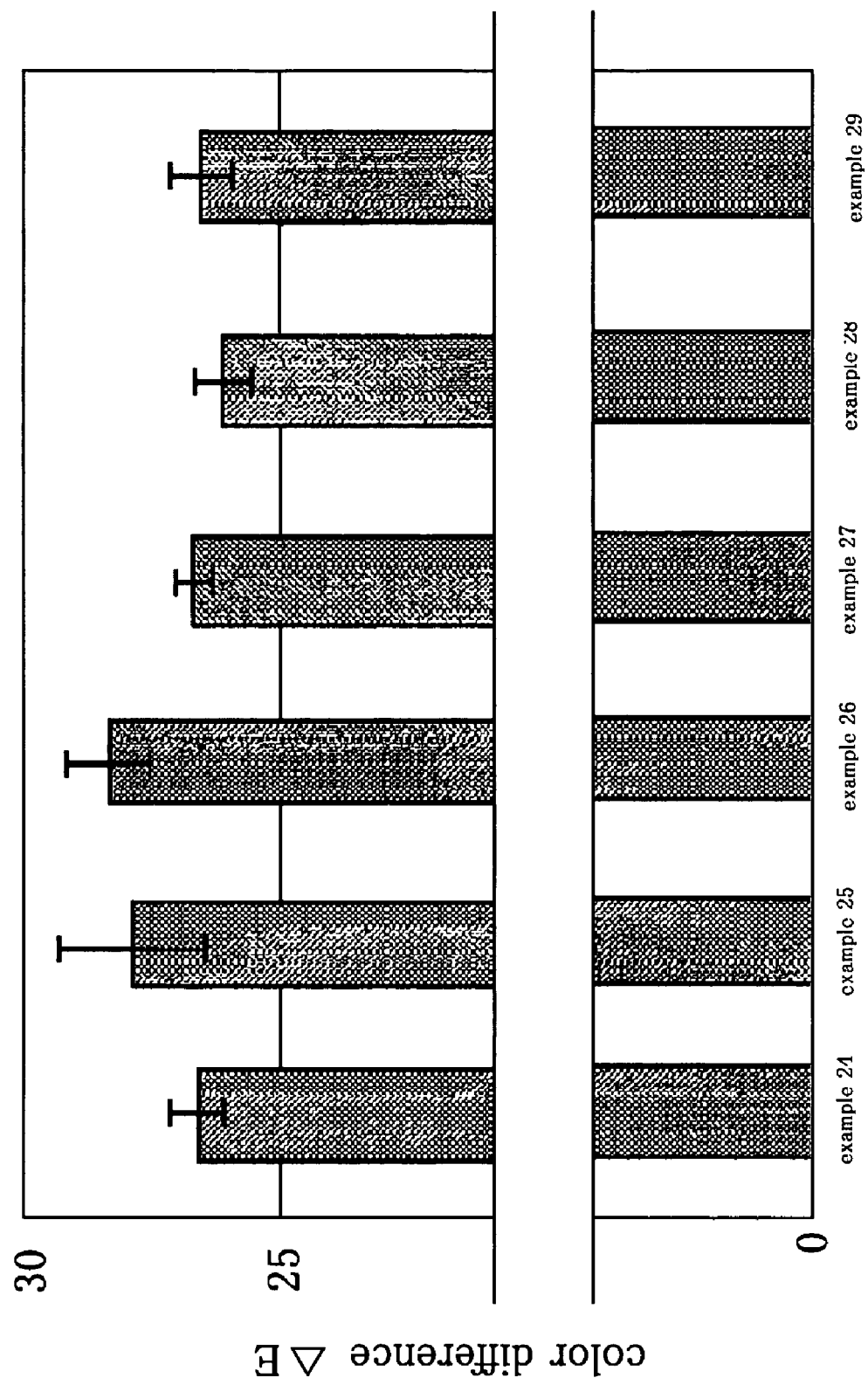
FIG. 2 shows the comparison of the relationship between the kind of the silicone and the dying performance.
Figure 3:
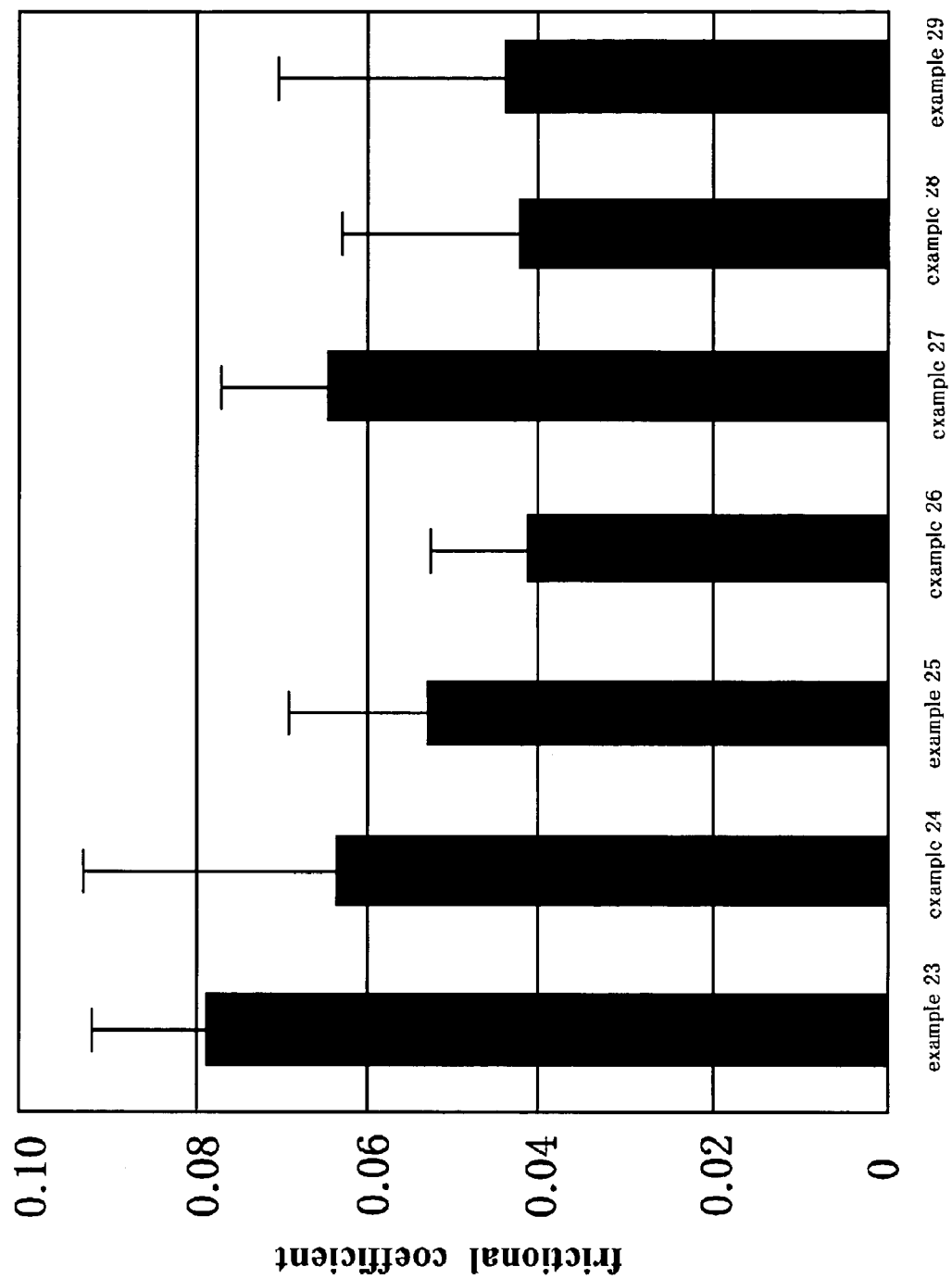
FIG. 3 shows the comparison of the relationship between the kind of the silicone and the frictional coefficient of the hair after dying operation.

The first agent and the second agent of the hair dye composition shown in Table 6 was mixed in the weight ratio of 1:1, and 8 g of the resultant mixture was applied onto 4 g of a goat hair bundle, allowed to stand at 30° C. for 30 minutes, rinsed thoroughly with warm water, shampooed, and then dried with a gentle air, and then examined for the color difference ΔE and the frictional coefficient. A larger ΔE reflects a higher dying performance, and a smaller frictional coefficient reflects a superior finish. The results are shown in FIGS. 2 and 3. The Example 23 is of non-treated control hairs.

TABLE 6

|  | Example | | | | | | |
|---|---|---|---|---|---|---|---|
|  | 24 | 25 | 26 | 27 | 28 | 29 | 30 |
| First agent (Cream state) | | | | | | | |
| Silicon | | | | | | | |
| Silicone rubber (*1) | — | 4.0 | — | — | — | — | — |
| Amino-modified polymer silicone rubber (*2) | — | — | 4.0 | — | — | — | 4.0 |
| Trimethylsiloxy silicate (*3) | — | — | — | 4.0 | — | — | — |
| Methyl phenyl poly siloxane (*4) | — | — | — | — | 4.0 | — | — |
| Amino-modified silicone oil (*5) | — | — | — | — | — | 4.0 | — |
| Stearyltrimethylammonium chloride | 2.0 | 2.0 | 2.0 | 2.0 | 2.0 | 2.0 | 2.0 |
| Cetyl alcohol | 7.0 | 7.0 | 7.0 | 7.0 | 7.0 | 7.0 | 7.0 |
| Stearyl alcohol | 3.0 | 3.0 | 3.0 | 3.0 | 3.0 | 3.0 | 3.0 |
| POE(20) cetyl ether | 0.2 | 0.2 | 0.2 | 0.2 | 0.2 | 0.2 | 0.2 |
| Monoethanolamine | 5.0 | 5.0 | 5.0 | 5.0 | 5.0 | 5.0 | — |
| Aqueous ammonia (28%) | — | — | — | — | — | — | 5.0 |
| Propylene glycol | 5.0 | 5.0 | 5.0 | 5.0 | 5.0 | 5.0 | 5.0 |
| Sodium dithionite | 0.1 | 0.1 | 0.1 | 0.1 | 0.1 | 0.1 | 0.1 |
| Disodium edentate dehydrate | 0.2 | 0.2 | 0.2 | 0.2 | 0.2 | 0.2 | 0.2 |
| Paraphenylendiamine | 1.0 | 1.0 | 1.0 | 1.0 | 1.0 | 1.0 | 1.0 |
| Resorcin | 0.5 | 0.5 | 0.5 | 0.5 | 0.5 | 0.5 | 0.5 |
| Paranitromethaphenylenediamine | 0.1 | 0.1 | 0.1 | 0.1 | 0.1 | 0.1 | 0.1 |
| Orange II | 0.05 | 0.05 | 0.05 | 0.05 | 0.05 | 0.05 | 0.05 |
| HC Red BN | 0.05 | 0.05 | 0.05 | 0.05 | 0.05 | 0.05 | 0.05 |
| Purified water | Remainder | | | | | | |
| Second agent (Liquid state) | | | | | | | |
| Hydrogen peroxide water (31%) | 16.0 | 16.0 | 16.0 | 16.0 | 16.0 | 16.0 | 16.0 |
| Methyl paraben | 0.1 | 0.1 | 0.1 | 0.1 | 0.1 | 0.1 | 0.1 |
| Phosphoric acid | 0.2 | 0.2 | 0.2 | 0.2 | 0.2 | 0.2 | 0.2 |
| Disodium hydrogenphosphate | 0.2 | 0.2 | 0.2 | 0.2 | 0.2 | 0.2 | 0.2 |
| Purified water | Remainder | | | | | | |
| Decolorizing performance | A | A | A | A | A | A | A |
| Dying performance | A | A | AA | A | A | A | A |
| Application performance | A | A | A | A | A | A | A |
| Hair touch | A | A | AA | A | A | A | A |
| Temporal stability | A | A | A | A | A | A | A |
| Irritative odor | A | A | A | A | A | A | C |

*1: Emulsion composition containing 30% by weight of highly polymerized dimethylpolysiloxane (average polymerization degree: 5000)
*2: Emulsion composition containing 15% by weight of highly polymerized dimethylsiloxane/methyl (aminopropyl) siloxane copolymer (dimethylsiloxane unit average polymerization degree: 10000, methyl(aminopropyl)siloxane unit average polymerization degree: 10)
*3: BY11-018 ™ (manufactured by Dow Corning Toray Silicone)
*4: SH556 ™ (manufactured by Dow Corning Toray Silicone)
*5: SF8452C ™ (manufactured by Dow Corning Toray Silicone)

As evident from FIG. 2, the Example 26 containing an amino-modified polymer silicone exhibited an extremely increased dying performance when compared with the Example 24 containing no silicone.

While it was revealed from FIG. 3 that any Example exhibited a lower frictional coefficient than that of the non-treated Example 23, the reduction in the frictional coefficient was extremely marked especially in the Example 26 containing an amino-modified polymer silicone when compared with the Example 24 containing no silicone.

It was further revealed by our tests that the dying performance promoting effect was imparted and a smoother finish was obtained especially when the amount of the amino-modified or ammonium-modified polymer silicone incorporated was 0.01 to 10.0% by weight, especially 0.1 to 7.0% by weight.

The Embodiments of a hair dye composition suitable for conducting the invention are exemplified below, but they do not restrict the technical scope of the invention in any way. Any of the hair dye compositions of the Embodiments had sufficient decolorizing performance and dying performance, exhibited no irritative odor and imparted an excellent smoothness of the hairs.

Embodiment 1

| Cream type hair dye | |
|---|---|
| (prescription) | weight % |
| First agent (Cream state) | |
| Monoethanolamine | 5.0 |
| Stearyltrimethylammonium chloride | 2.0 |
| Cetyl alcohol | 7.0 |
| Stearyl alcohol | 3.0 |
| POE(20) octhyl dodecylether | 0.2 |
| Hexylene glycol | 3.0 |
| Squalane | 5.0 |
| Amino-modified polymer silicone (SM8702C ™: manufactured by Dow Corning Toray Silicone) | 2.0 |
| Collagen protein hydrolyzate | 2.0 |
| Wild oat extract | 0.1 |
| Sodium dithionite | 0.1 |
| Disodium edentate dehydrate | 0.2 |
| Paraphenylendiamine | 1.0 |
| Resorcin | 0.5 |
| 2,4-diaminophenoxyethanol chlorate | 0.1 |
| Purified water | Remainder |
| Second agent (Cream state) | |
| Hydrogen peroxide water (31%) | 16.0 |
| Stearyltrimethylammonium chloride | 2.0 |
| Cetyl alcohol | 7.0 |
| Stearyl alcohol | 3.0 |
| POE(20)octhyl dodecyl ether | 0.2 |
| Methylparaben | 0.1 |
| Phosphoric acid | 0.2 |
| Disodium hydrogenphosphate | 0.2 |
| Purified water | Remainder |

Mixing ratio First agent:Second agent = 1:1
Higher alcohol/Quaternary ammonium salt cationic surfactant (Molar ratio) = 6.96

Embodiment 2

| Emulsion type hair dye | |
|---|---|
| (prescription) | weight % |
| First agent (Cream state) | |
| Monoethanolamine | 6.0 |
| Monopropanol amine | 3.0 |
| Behenyltrimethylammonium chloride | 2.4 |
| Stearyl alcohol | 8.0 |
| POE(20) stearyl ether | 1.2 |
| Isoprene glycol | 3.0 |
| Polyethylene glycol | 5.0 |
| High polymerized dimethylpolysiloxane | 0.5 |
| Keratin protein hydrolyzate | 2.0 |
| Jojoba alcohol | 0.1 |
| Urea | 0.5 |
| Sodium dithionite | 0.1 |
| Disodium edentate dehydrate | 0.2 |
| Toluene-2,5-diamine | 0.5 |
| Orange II | 0.1 |
| HC RED BN | 0.05 |
| Paranitro meta phenylenediamine sulfate | 0.1 |
| Purified water | Remainder |
| Second agent (Emulsion state) | |
| Hydrogen peroxide water (35%) | 14.0 |
| Behenyltrimethylammonium chloride | 0.2 |
| Stearyl alcohol | 2.0 |
| POE(4) cetyl ether | 0.1 |
| Phenacetin | 0.1 |
| Disodium edentate dehydrate | 0.2 |
| Phosphoric acid | 0.2 |
| Purified water | Remainder |

Mixing ratio First agent:Second agent =1:2
Higher alcohol/ Quaternary ammonium salt cationic surfactant (Molar ratio) = 10.03

Embodiment 3

| Emulsion type hair dye | |
|---|---|
| (prescription) | weight % |
| First agent (Emulsion state) | |
| Monoethanolamine | 4.0 |
| Aqueous ammonia | 0.7 |
| Distearyldimethylammonium chloride | 1.0 |
| Cetyl alcohol | 3.5 |
| Stearyl alcohol | 1.5 |
| Propylene glycol | 10.0 |
| Fluid paraffin | 2.0 |
| Cationized hydroxyethyl cellulose | 0.5 |
| Glycerol monostearate | 1.0 |
| Cyclic silicone pentamer oligomer | 5.0 |
| Sodium dithionite | 0.1 |
| Soybean lecithin | 0.5 |
| Disodium edentate dehydrate | 0.2 |
| Paranitroortho phenylendiamine | 1.0 |
| Basic Brown 16 | 0.05 |
| HC Orange | 0.05 |
| Purified water | Remainder |
| Second agent (Emulsion state) | |
| Hydrogen peroxide water (35%) | 16.0 |
| Distearyldimethylammonium chloride | 1.0 |
| Cetyl alcohol | 1.0 |
| Stearyl alcohol | 1.0 |
| Methylparaben | 0.1 |

-continued

Emulsion type hair dye

| (prescription) | weight % |
|---|---|
| Phosphoric acid | 0.2 |
| Disodium hydrogenphosphate | 0.2 |
| Purified water | Remainder |

Mixing ratio First agent:Second agent = 1:1.5
Higher alcohol/ Quaternary ammonium salt cationic surfactant (Molar ratio) = 4.59

Embodiment 4

Aerosol bubble hair dye

| (prescription) | weight % |
|---|---|
| First agent | |
| Monoethanolamine | 4.0 |
| Ammonium chloride | 2.0 |
| Cetyltrimethylammonium chloride | 0.3 |
| Cetyl alcohol | 1.5 |
| POE(10) lauryl ether | 0.2 |
| Vaseline | 3.0 |
| Glycerin | 12.0 |
| Hydroxyethyl cellulose hydroxyethyl propyl trimethylammonium chloride ether | 0.2 |
| Sodium dithionite | 0.1 |
| Disodium edentate dehydrate | 0.2 |
| Paraphenylendiamine | 1.0 |
| Resorcin | 0.5 |
| Purified water | Remainder |
| Second agent | |
| Hydrogen peroxide water (35%) | 16.0 |
| Stearyltrimethylammonium chloride | 0.5 |
| Cetyl alcohol | 2.0 |
| POE(20) octhyl dodecyl ether | 0.2 |
| Methylparaben | 0.1 |
| Phosphoric acid | 0.2 |
| Disodium hydrogenphosphate | 0.2 |
| Purified water | Remainder |

*To the stock solution described above, a propellant LPG (5.0 kg/cm³; 25° C.) was filled in the ratio of 94:6 to obtain the first agent and the second agent of an aerosol foam-type hair dye.
Mixing ratio: First agent:Second agent = 1:1
Higher alcohol/quaternary ammonium salt cationic surfactant (molar ratio) = 6.17

Embodiment 5

| (prescription) | weight % |
|---|---|
| First agent (Cream state) | |
| Monoethanolamine | 4.0 |
| Aqueous ammonia (28%) | 0.5 |
| Stearyltrimethylammonium chloride | 2.0 |
| Cetyl alcohol | 7.0 |
| Stearyl alcohol | 3.0 |
| POE(20) cetyl ether | 0.2 |
| Hexylene glycol | 3.0 |
| Jojoba alcohol | 2.0 |
| Amino-modified polymer silicone | 2.0 |

-continued

| (prescription) | weight % |
|---|---|
| Collagen protein hydrolyzate | 2.0 |
| Ascorbic acid | 0.2 |
| Sodium dithionite | 0.1 |
| Disodium edentate dehydrate | 0.2 |
| Paraphenylenediamine | 0.8 |
| Resorcin | 0.5 |
| Orthoaminophenol | 0.3 |
| Purified water | Remainder |
| Second agent (Cream state) | |
| Hydrogen peroxide water (35%) | 16.0 |
| Stearyltrimethylammonium chloride | 2.0 |
| Cetyl alcohol | 7.0 |
| Stearyl alcohol | 3.0 |
| POE(20) octhyl dodecyl ether | 0.2 |
| Methyl paraben | 0.1 |
| Phosphoric acid | 0.2 |
| Disodium hydrogenphosphate | 0.2 |
| Purified water | Remainder |

Mixing ratio First agent:Second agent = 1:1
Higher alcohol/ Quaternary ammonium salt cationic surfactant (Molar ratio) = 6.96

What is claimed is:

1. A hair dye composition comprising:
   a first agent containing an alkanolamine and an oxidation dye; and,
   a second agent containing an oxidant,
   wherein two or more different higher alcohols selected from the group consisting of lauryl alcohol, myristyl alcohol, cetyl alcohol, cetanol, stearyl alcohol, cetostearyl alcohol, behenyl alcohol, 2-octyldodecanol and oleyl alcohol and a quaternary ammonium salt cationic surfactant selected from the group consisting of stearyltrimethylammonium chloride, behenyltrimethylammonium chloride and distearyldimethylammonium chloride, are contained in the first agent and/or the second agent;
   wherein the molar ratio of the two or more different higher alcohols to the quaternary ammonium salt cationic surfactant is in the range of 3 to 15.

2. The hair dye composition according to claim 1 wherein substantially no ammonia is contained.

3. The hair dye composition according to claim 1,
   wherein a polyoxyethylene alkyl ether nonionic surfactant are further contained in the first agent and/or the second agent;
   wherein the weight of the polyoxyethylene alkyl ether nonionic surfactant incorporated in each of the first agent and the second agent is less than the weight of the quaternary ammonium salt cationic surfactant incorporated.

4. The hair dye composition according to claim 2,
   wherein a polyoxyethylene alkyl ether nonionic surfactant are further contained in the first agent and/or the second agent;
   wherein the weight of the polyoxyethylene alkyl ether nonionic surfactant incorporated in each of the first agent and the second agent is less than the weight of the quaternary ammonium salt cationic surfactant incorporated.

5. The hair dye composition according to claim 1 comprising the quaternary ammonium salt cationic surfactant in an amount of 0.05 to 5.0% by weight based on the entire composition.

6. The hair dye composition according to claim 2 comprising the quaternary ammonium salt cationic surfactant in an amount of 0.05 to 5.0% by weight based on the entire composition.

7. The hair dye composition according to claim 1, further comprising, in the first agent and/or the second agent, an amino-modified polymer silicone or ammonium-modified polymer silicone represented by Formula (I):

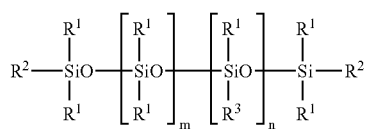

wherein $R^1$ is a methyl group or partly a phenyl group, $R^2$ is the same as $R^3$ or a methyl group or a hydroxyl group, $R^3$ is an amino group- or ammonium group-containing substituent represented by Formula $R^4Z$ wherein $R^4$ is a divalent alkylene group having 3 to 6 carbon atoms, Z is a monovalent group selected from the group consisting of $-NR^5{}_2$, $-N^+R^5{}_3A$, $-NR^5(CH_2)_aNR^5{}_2$, $-NR^5(CH_2)_aN^+R^5{}_3A$ and $-NR^5(CH_2)_aN(R^5)C=O(R^6)$ wherein $R^5$ is a hydrogen or an alkyl group having 1 to 4 carbon atoms, $R^6$ is an alkyl group having 1 to 4 carbon atoms, A is Cl, Br or I, and a is an integer of 2 to 6, and each of m and n is a positive integer and m+n is an integer of 3000 to 20000, and n/m is 1/500 to 1/10000.

8. The hair dye composition according to claim 2 further comprising, in the first agent and/or the second agent, an amino-modified polymer silicone or ammonium-modified polymer silicone represented by Formula (I):

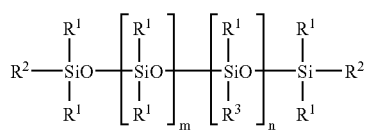

wherein $R^1$ is a methyl group or partly a phenyl group, $R^2$ is the same as $R^3$ or a methyl group or a hydroxyl group, $R^3$ is an amino group- or ammonium group-containing substituent represented by Formula $R^4Z$ wherein $R^4$ is a divalent alkylene group having 3 to 6 carbon atoms, Z is a monovalent group selected from the group consisting of $-NR^5{}_2$, $-N^+R^5{}_3A$, $-NR^5(CH_2)_aNR^5{}_2$, $-NR^5(CH_2)_aN^+R^5{}_3A$ and $-NR^5(CH_2)_aN(R^5)C=O(R^6)$ wherein $R^5$ is a hydrogen or an alkyl group having 1 to 4 carbon atoms, $R^6$ is an alkyl group having 1 to 4 carbon atoms, A is Cl, Br or I, and a is an integer of 2 to 6, and each of m and n is a positive integer and m+n is an integer of 3000 to 20000, and n/m is 1/500 to 1/10000.

9. A hair dye composition comprising:
a first agent containing an alkanolamine and an oxidation dye; and,
a second agent containing an oxidant,
wherein two or more different higher alcohols and a quaternary ammonium salt cationic surfactant are contained in the first agent and/or the second agent;
wherein said quaternary ammonium salt cationic surfactant is a monoalkyl quaternary ammonium salt represented by formula (II):

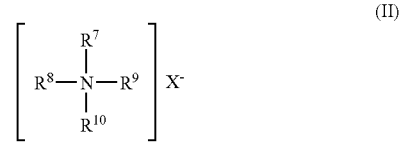

wherein $R^7$ is a straight or branched alkyl group having 8 to 36 carbon atoms which may be substituted by a hydroxyl group, $R^8$, $R^9$ and $R^{10}$ are the same or different, and each is an alkyl group having 1 to 3 carbon atoms or benzyl group which may be substituted by a hydroxyl group, and X is a halogen atom or an alkyl sulfate group having 1 to 2 carbon atoms; or a dialkyl quaternary ammonium salt represented by Formula (III):

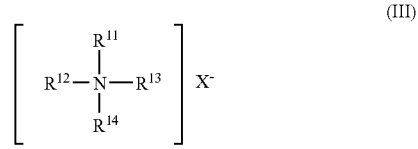

wherein $R^{11}$ and $R^{12}$ are the same or different and each is a straight or branched alkyl group having 8 to 36 carbon atoms which may be substituted by a hydroxyl group, $R^{13}$ and $R^{14}$ are the same or different, and each is an alkyl group having 1 to 3 carbon atoms or benzyl group which may be substituted by a hydroxyl group, and X is a halogen atom or an alkyl sulfate group having 1 to 2 carbon atoms; and wherein the molar ratio of two or more different higher alcohols to the quaternary ammonium salt cationic surfactant is in the range of 3 to 15.

10. The hair dye composition according to claim 9, wherein said quaternary ammonium salt cationic surfactant does not contain an epoxyalkyl substitutent or a halohydrin substituent.

11. The hair dye composition according to claim 9, wherein said quaternary ammonium salt cationic surfactant is stearyltrimethylammonium chloride, behenyltrimethylammonium chloride, or distearyldimethylammonium chloride.

12. The hair dye composition according to claim 9, wherein said hair dye composition contains substantially no ammonia.

13. The hair dye composition according to claim 9, wherein said higher alcohols are at least two selected from the group consisting of lauryl alcohol, myristyl alcohol, cetyl alcohol, cetanol, stearyl alcohol, cetostearyl alcohol, behenyl alcohol, 2-octyldodecanol, and oleyl alcohol.

* * * * *